United States Patent
Mogan et al.

[11] Patent Number: 5,870,186
[45] Date of Patent: Feb. 9, 1999

[54] DETECTOR FOR PARTICLE SURFACE CONTAMINATION

[75] Inventors: Paul A. Mogan, Winter Park; Christian J. Schwindt, Oviedo; Carl B. Mattson, Titusville, all of Fla.

[73] Assignee: The United States of America as represented by the Administrator National Aeronautics and Space Administration, Washington, D.C.

[21] Appl. No.: 903,196

[22] Filed: Jul. 15, 1997

[51] Int. Cl.⁶ .......................... G01N 21/00; G01N 15/02
[52] U.S. Cl. ........................ 356/237; 356/335; 250/573
[58] Field of Search .................... 356/237, 239, 356/338, 335–337, 339–343, 430, 431; 250/573, 571, 574, 221, 222.1

[56] References Cited

U.S. PATENT DOCUMENTS

| | | | |
|---|---|---|---|
| 4,526,468 | 7/1985 | Stegmeier et al. | 356/338 |
| 4,825,094 | 4/1989 | Borden et al. | 356/338 |
| 5,218,211 | 6/1993 | Cresswell et al. | 250/571 |
| 5,245,403 | 9/1993 | Kato et al. | 356/257 |
| 5,268,735 | 12/1993 | Hayashi | 356/239 |
| 5,412,221 | 5/1995 | Curtis et al. | 356/338 |
| 5,438,408 | 8/1995 | Weichert et al. | 356/336 |
| 5,455,675 | 10/1995 | Witt et al. | 356/336 |
| 5,471,298 | 11/1995 | Moriya | 356/336 |
| 5,471,299 | 11/1995 | Kaye et al. | 356/336 |
| 5,491,642 | 2/1996 | Wormell et al. | 364/509 |

*Primary Examiner*—Hoa Q. Pham
*Attorney, Agent, or Firm*—Beth A. Vrioni

[57] ABSTRACT

A system and method for detecting and quantizing particle fallout contamination particles which are collected on a transparent disk or other surface employs an optical detector, such as a CCD camera, to obtain images of the disk, and a computer for analyzing the images. From the images, the computer detects, counts and sizes particles collected on the disk. The computer also determines, through comparison to previously analyzed images, the particle fallout rate, and generates an alarm or other indication if the rate exceeds a maximum allowable value. The detector and disk are disposed in a housing having an aperture formed therein for defining the area on the surface of the disk which is exposed to the particle fallout. A light source is provided for evenly illuminating the disk. A first drive motor slowly rotates the disk to increase the amount of its surface area which is exposed through the aperture to the particle fallout. A second motor is also provided for incrementally scanning the disk in a radial direction back and forth over the camera so that the camera eventually obtains images of the entire surface of the disk which is exposed to the particle fallout.

26 Claims, 4 Drawing Sheets

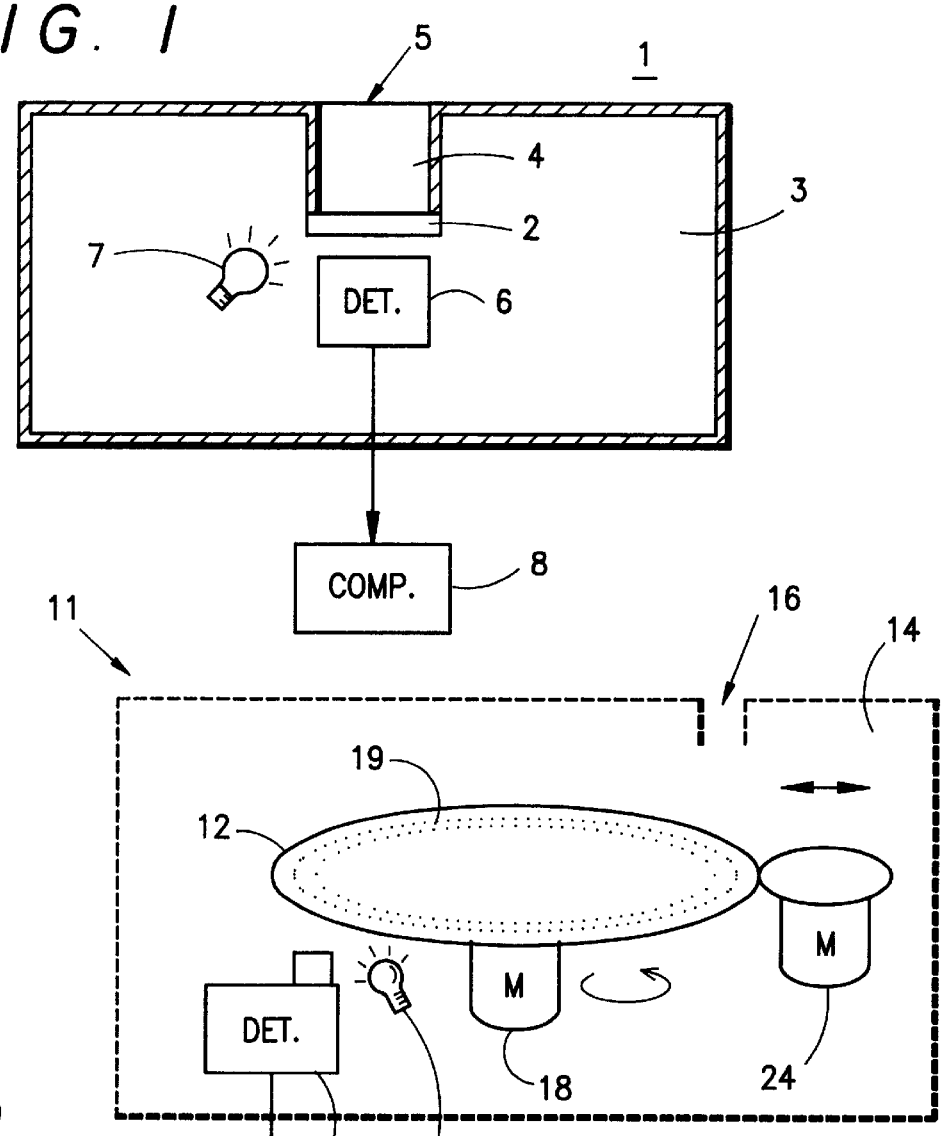
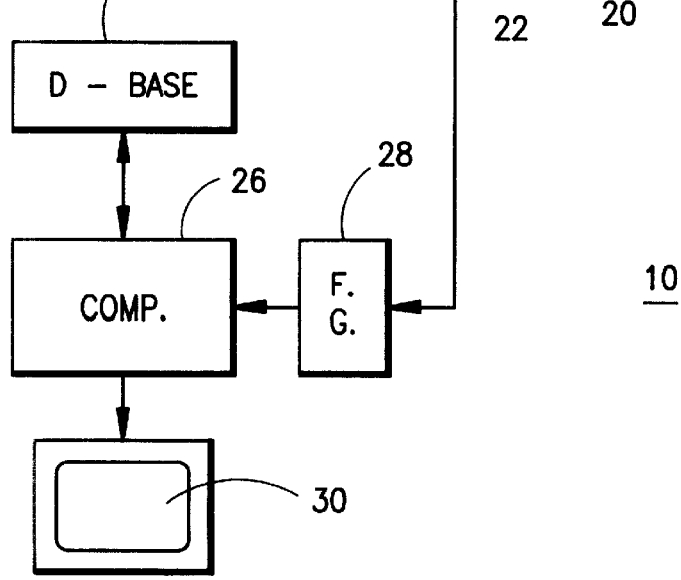
FIG. 1
FIG. 2

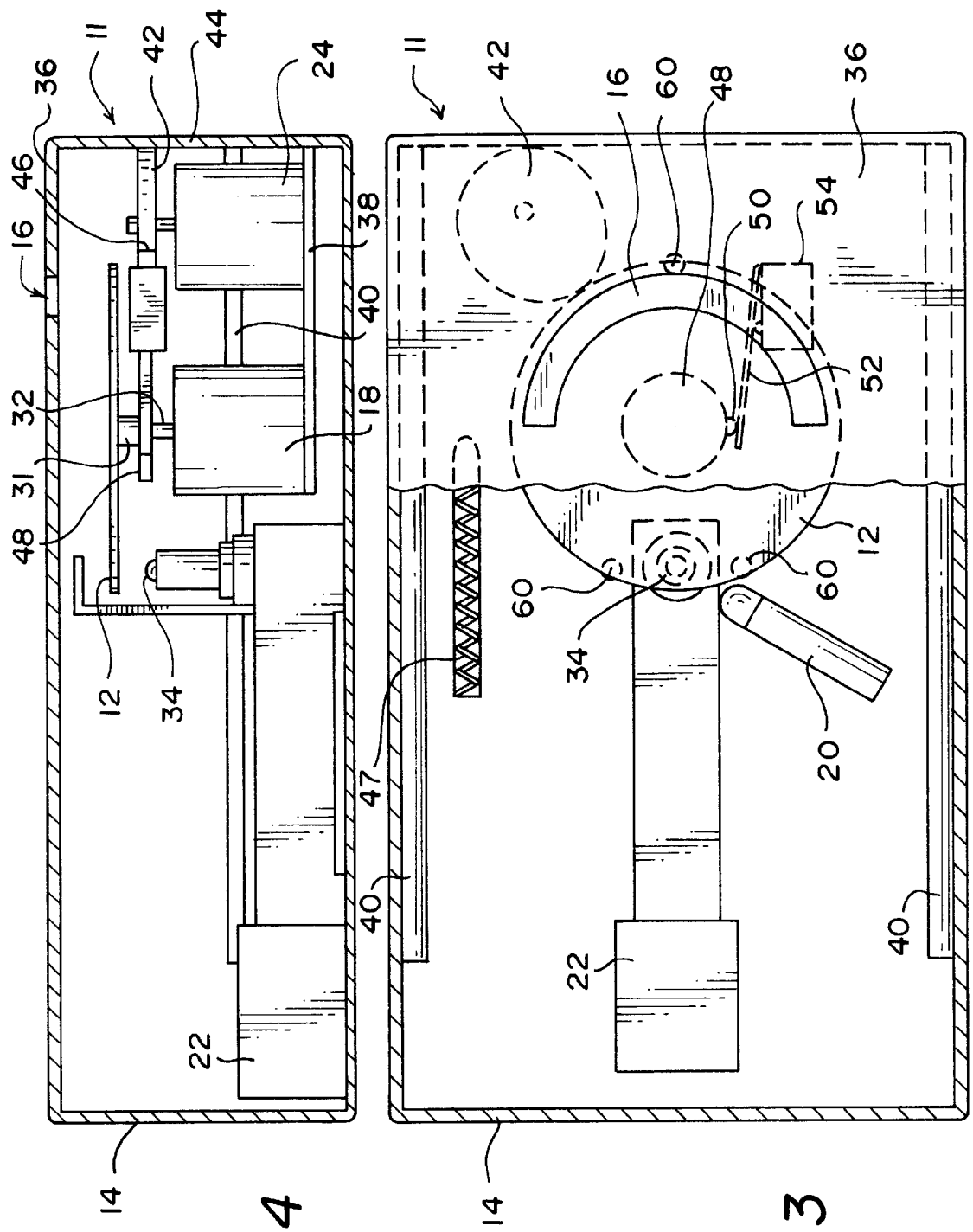

FIG. 5
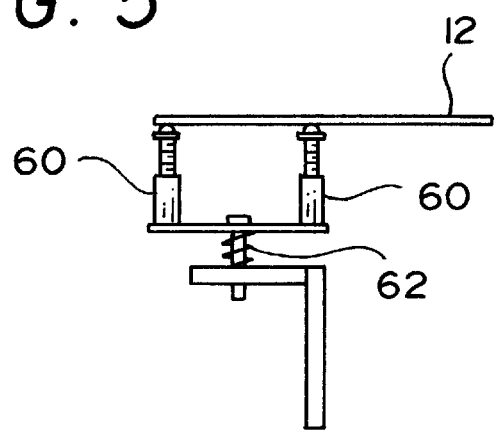
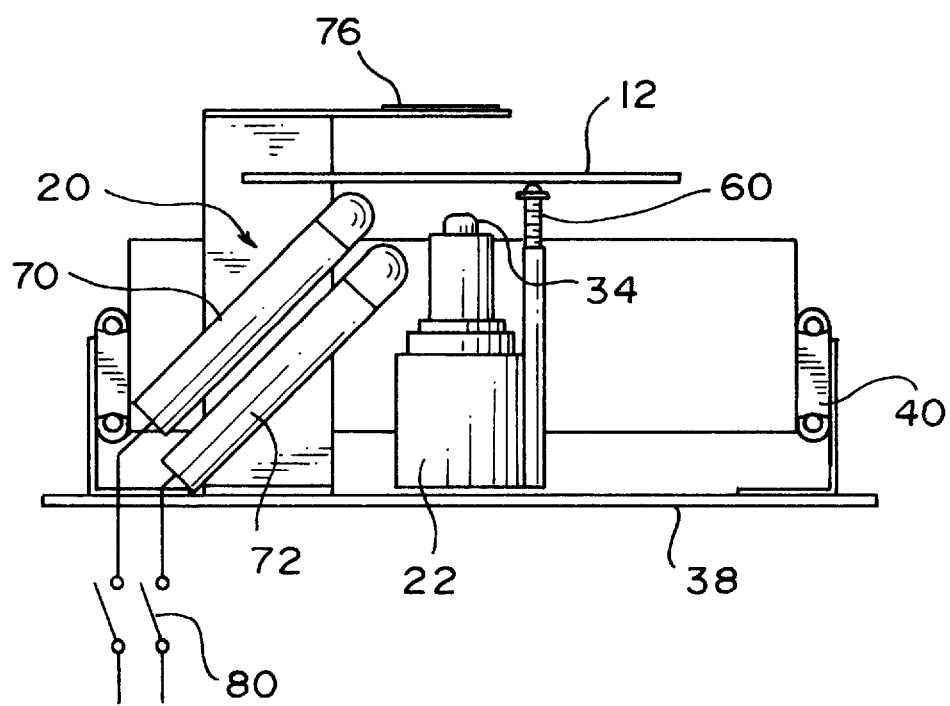
FIG. 6

DETECTOR FOR PARTICLE SURFACE CONTAMINATION

DETECTOR FOR PARTICLE SURFACE CONTAMINATION ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 U.S.C. 2457).

BACKGROUND OF THE INVENTION

The present invention relates in general to a system and method for detecting, quantizing and classifying particle fallout contamination.

Many facilities, such as clean rooms, require monitoring of particle fallout contamination to insure that the facilities maintain a desired cleanliness level. One known cleanliness monitoring technique used by the aerospace industry employs a gridded witness filter which is placed in the clean work area so that fallout particles will be deposited thereon. After a predetermined time interval, the filter is taken to a laboratory where the particles are manually counted, sized and classified. This technique has a number of disadvantages. First, handling of the witness filter can easily change the sample prior to analysis through disruption of the deposited particles, or collection of additional particles not attributable to the work area. Second, the measurement is in no way real-time, and thus cannot provide any indication of severe contamination, for example, as it occurs. Finally, the need for manually counting the collected particles requires a large amount of labor and is highly susceptible to human errors.

Instruments also exist which are based on side-scattered light measurement or on particles falling through a laser grid and interrupting the laser beam, thereby producing a pulse of light which is counted. Although these instruments eliminate the need for manual particle counting, the instruments do not actually image the particles, and at best produce only an estimate of the number of particles and their sizes.

A need therefore exists for a particle surface contamination detector which can automatically provide analysis of fallout particle numbers and sizes, as well as real-time measurements of particle fallout rates.

SUMMARY OF THE INVENTION

The present invention satisfies the foregoing need through provision of a system and method for detecting and quantizing particle fallout contamination which is fully automated, has real-time detection capabilities, and reliably counts, sizes and classifies collected particles. More particularly, the system employs a flat, smooth, transparent particle collection surface which is disposed in a housing. A sized aperture is formed in the top of the housing over a portion of the transparent collection surface to allow particle fallout to collect thereon.

Disposed beneath the surface in the housing is an optical detector, such as a camera, which images the particles. A light source is also preferably disposed in the housing for illuminating the surface so that particles collected thereon may be easily imaged by the detector. The image signals generated by the optical detector are read by a computer which contains particle detection, sizing, counting and classifying algorithms for analyzing the particle fallout. The algorithms make these calculations in real-time so that particle fallout rate at any given moment can be calculated, and a warning or indication can be generated if the rate exceeds a predetermined threshold.

In a preferred embodiment of the present invention, the particle collection surface is the top surface of a rotatable circular disk, such as a transparent unprinted CD, for example, which is rotated by a first drive motor at a slow speed (e.g., 1 rpm), so that the particle fallout is collected over a larger surface area than that defined by the aperture in the housing. This feature of the invention helps insure that stacking of the collecting particles will be minimized, thereby reducing any measurement inaccuracies which are generated thereby. The disk and drive motor are preferably mounted in a movable drawer type subassembly within the housing. A second motor is provided which drives a cam element that moves the subassembly linearly back and forth in increments over the camera to facilitate random sampling of different portions of the disk's collection surface. After these random samples have been taken for a sufficient period of time (e.g., half an hour), an analysis can be made about the contamination present on the surface of the disk.

BRIEF DESCRIPTION OF THE DRAWINGS

The features and advantages of the present invention will become apparent from the following detailed description of a preferred embodiment thereof, taken in conjunction with the accompanying drawings, in which:

FIG. 1 is a schematic illustration of a particle surface contamination detector system constructed in accordance with fundamental concepts of the present invention;

FIG. 2 is a schematic illustration of a particle surface contamination detector system constructed in accordance with a preferred embodiment of the present invention;

FIG. 3 is a schematic illustration showing the top view of a detector assembly (with a top cover removed) constructed in accordance with a preferred embodiment of the present invention;

FIG. 4 is a cross sectional side view of the assembly illustrated in FIG. 3;

FIG. 5 is a schematic illustration of a focusing mechanism employed in the assembly of FIG. 3 for positioning a particle collection disk relative to an optical detector;

FIG. 6 is a schematic illustration showing a lighting arrangement for illuminating the particle collection disk in the preferred embodiment of the present invention.

DETAILED DESCRIPTION OF THE PREFERRED EMBODIMENT

Figure 7:
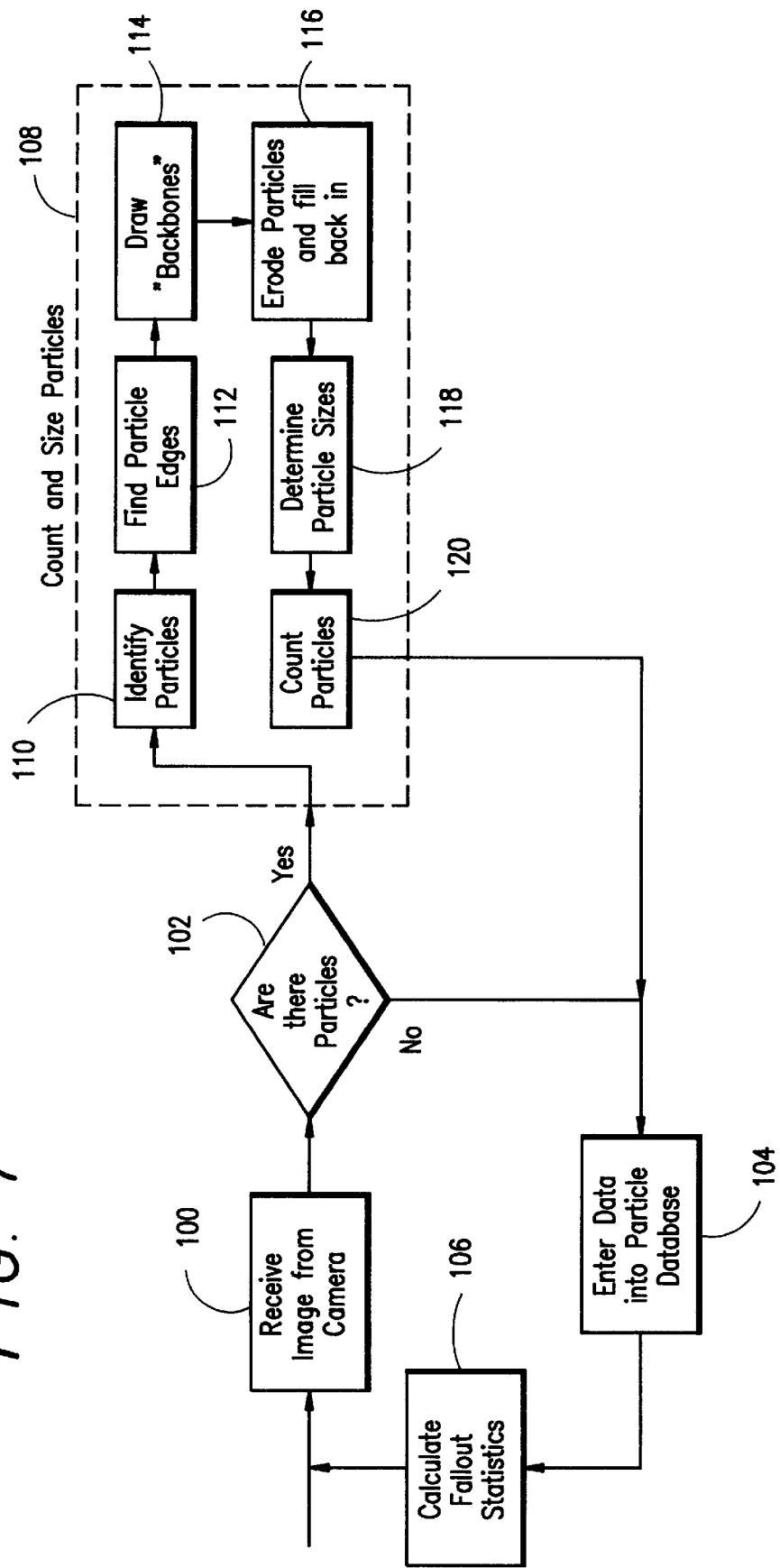
FIG. 7 is a flow chart illustrating the method implemented by the preferred embodiment's algorithms for imaging, counting and sizing collected particles.

FIG. 1 illustrates a particle surface contamination detection system 1 which is constructed in accordance with the fundamental concepts of the present invention. The system 1 includes a flat transparent particle collection surface 2, which may be a witness plate, for example, that is disposed in an opaque housing 3 beneath a chimney 4 having a sized aperture 5 for directing particle fallout onto a predetermined area of the collection surface 2.

An optical detector 6 is positioned beneath the collection surface 2 for generating an image of the particles collected thereon. A light source 7 is provided for illuminating the witness plate 2 so that particles collected thereon can be imaged by the detector 6. The images from the detector 6 are input to a computer 8 which detects particles in the image, and counts, sizes and classifies them using algorithms which are discussed in greater detail in conjunction with FIG. 7. The computer 8 preferably analyzes images from the detector 6 on a periodic basis to facilitate particle fallout rate calculations in virtually real-time.

With reference to FIG. 2, a particle surface contamination detection system 10 is illustrated which is constructed in accordance with a preferred embodiment of the present invention, and also incorporates the basic features of the system 1 of FIG. 1. The system 10 includes a particle collection and detection assembly 11 comprising the following elements. A smooth, flat, transparent disk 12 is provided as the surface for collecting particle fallout to be detected and quantized. In the preferred embodiment of the present invention, the disk 12 comprises an unprinted or blank compact disk (CD). Information is recorded on a CD by printing or depositing a reflective metal layer thereon. However, a blank CD is transparent, and is thus perfectly suited for this application in view of its extremely smooth, flat and transparent surface. It will be understood, however, that any smooth, flat and transparent surface may be employed as the collection surface.

The disk 12 is preferably contained within an opaque housing 14 which has a sized aperture 16 disposed in a top thereof for directing particles onto a portion of the disk 12. More specifically, the aperture 16 has a predetermined cross sectional area which defines the area of the disk 12 on which the particles can fall.

Preferably, the disk 12 is rotatable at a slow speed (e.g., 1 rpm) by a drive motor 18 so that an entire circumferential collection band 19 on the surface of the disk 12 is utilized to collect the particle fallout. In this regard, a CD is also particularly suited for rotation by the drive motor 18. The drive motor 18 is preferably a gear or stepper motor which provides precise control of the disk's rotation. The foregoing feature of the invention minimizes the likelihood that particles will be stacked on top of one another during a given measurement interval. It should be understood that in clean room environments where the system 10 is intended to be employed, the normal amount of particle fallout is very small so that it is unlikely that any particle stacking will occur if a large portion of the disk's surface is utilized.

A light source 20 of any suitable type is positioned in the housing 14 to provide even illumination of the disk 12. The light source 20 is discussed in greater detail later in conjunction with FIG. 6. An optical detection device, such as a CCD camera 22 and associated collection optics, is positioned in the housing 14 beneath a portion of the disk 12 to generate an image of the particle fallout thereon. A second drive motor 24, which is preferably a stepper motor, incrementally moves the disk 12 back and forth over the camera 22 so that the entire exposed collection band 19 of the disk 12 is eventually scanned thereby. A power supply 25 (e.g. transformer, battery, etc.) is provided for powering all of the system elements requiring electricity for operation.

The image data generated by the camera 22 is input to a conventional computer 26 which, as discussed in greater detail later in conjunction with FIG. 7, executes an algorithm that periodically analyzes the images acquired from the camera 22 by a frame grabber board 28 to determine the amount, size and type of particle fallout, as well as the fallout rate. The computer 26 stores all of the measurements and calculations in a database 29, and generates appropriate reports on a monitor 30, or other suitable output device (e.g. printer). In addition, the computer system 26 can generate real-time visual warnings or alarms on the monitor 30 in the event that a particle fallout rate has been detected to exceed a maximum allowable rate. This is particularly useful for providing rapid detection and indication of severe contamination conditions which may occur, for example, if contamination prevention measures in a clean work area fail.

FIGS. 3 and 4 show the details of the particle collection and detection assembly 11 which is employed in the preferred embodiment of the present invention. The particle collection disk 12 is mounted by means of a flexible coupling 31 on a spindle 32 of the first drive motor 18. A microscope objective 34 is positioned beneath the disk 12 which magnifies the images of the disk 12 before they are received by the camera 22.

As illustrated in FIG. 3, the aperture 16 is formed in an aperture plate 36 of the housing 14, has a generally semicircular shape, and exposes a portion of the collection band 19 on the disk 12 which is generally opposite the position of the microscope objective 34. Since the microscope objective 34 acquires an image of only a small portion of the total width of the particle collection band 19 on the disk 12, the first and second drive motors 18 and 24, disk 12 and aperture plate 36 are mounted in a separate drawer type subassembly 38 which can be slid back and forth along a pair of conventional drawer slides 40 to facilitate lateral movement of the disk 12 relative to the microscope objective 34. This enables the microscope objective 34 to be focused on different radial sectors of the collection band 19. An irregular shaped, eccentric cam member 42 is driven by the second drive motor 24 to provide this lateral movement by engaging a cover member 44 of the housing 14, and a vertical surface 46 of the subassembly 38. A spring loaded plunger mechanism 47 is provided for biasing the subassembly 38 against the first cam member 42.

To provide intermittent operation of the second drive motor 24 for indexing the cam member 42, a second cam member 48 is driven by the first motor 18 which includes a bump 50 that engages an actuating lever 52 of a micro switch 54 once for every revolution of the first drive motor 18. The micro switch 54 controls actuation of the second drive motor 24 so that the first cam member 42 is rotated for a few seconds for every revolution of the first drive motor 18. This incrementally moves the disk 12 radially or laterally so that the microscope objective 34 images a different radial sector of the collection band 19 on the disk 12 for each image acquired by the video camera 22. The irregular surface of the first cam member 42 insures that a slightly different radial sector of the disk 12 will be imaged each time by the camera 22. It should be understood that the second drive motors 24 and cam member 42 could be replaced by any other type of suitable linear actuator if desired.

As illustrated in FIG. 5, a focusing mechanism is provided for maintaining the distance between disk 12 and the microscope objective 34 constant, and providing a means for adjusting its distance. In particular, the disk 12 is supported by a plurality of support screws 60 which maintain the disk 12 level at all times. A focus adjusting screw 62 is also provided for adjusting the vertical position of the disk 12 relative to the microscope objective 34. The flexible coupling 31 insures that irregular movement of the spindle 32 will not affect the focus adjustment as the disk 12 rotates.

As illustrated best in FIG. 6, the light source 20 in the preferred embodiment actually comprises first and second incandescent light sources, e.g., flashlights, 70 and 72. The first light source 70 is employed for back lighting the top surface of the disk 12 through diffusion of light off of a diffuser 76, and the second light source 72 provides front lighting of the bottom surface of the disk 12. A pair of switches 80 is provided for selectively actuating one or the other of the light sources 70 or 72 to provide the desired illumination of the disk surface. The use of two light sources provides added versatility by enabling the imaged particles to be made either lighter or darker than the background, depending on the light source selected. More specifically, use of the back lighting light source 70 causes the particles to show up as dark spots on the disk 12, while use of the front lighting light source 72 causes the particles to show up as light spots on the disk 12.

FIG. 7 is a flow chart which illustrates the algorithm implemented by the computer system 26 to analyze the image data generated by the camera 22. The first step illustrated at 100 is to receive a digital image from the camera 22. The computer 26 does this by periodically sampling the data in the frame grabber board 28. Since the particle fallout rate in a typical clean room is very low, image sampling need not occur very frequently to provide sufficient precision for the detection and analysis. In the preferred embodiment, however, the computer 26 samples or reads the image data in the frame grabber board 28 as soon as the computer 26 is finished analyzing the previous image. Thus, a new image is analyzed every few seconds or less, depending on the number of detected particles in the previous image, and this improves statistical analysis capabilities, and alarm condition responsiveness. It will be understood, however, that any other suitable measurement interval could be employed as desired.

After the image is received, the first analysis step as illustrated at 102 is to determine if any particles are detected in the image. If not, no further inquiry is necessary, the data for this reading is entered into the particle database 29 at step 104, and fallout statistics are calculated at step 106. If particles are detected in the image, the computer 26 initiates a counting and sizing process at step 108. First, the particles are identified at step 110 using any suitable conventional image analysis which can discriminate particles in the image. Once all particles have been identified, the algorithm locates the edges of the particles at step 112, and then draws at step 114 a "backbone" along the center length of each particle to provide a measure of the length of each particle. This is an important step in the analysis of particles having curled shapes, for example, and for the classification of fiber type particles (i.e., particles whose length to width ratio is greater than or equal to 10:1). Next, at step 116, the image of each particle is eroded away on either side of the backbone, and is then filled back in to eliminate any "holes" or clear spots which were present in the original particle image that could create inaccuracies in their size determination. The size of each particle is determined next at step 118, and then the number of particles in each of a number of size ranges is counted at step 120. In the preferred embodiment of the present invention, the particles may be classified or categorized in any desired manner, such as by area, length, type, shape, etc. As an example, one U.S. Government standard categorizes the particles into the following lengths: 10–20 microns, 20–50 microns, 50–100 microns, 100–250 microns, and over 250 microns.

The particle analysis data is entered into the database 29 at step 104, and the fallout statistics are calculated at step 106. The post processing which is carried out at step 106 serves to calculate the area coverage for the particles on the disk 12, and the total accumulated area imaged, and stores this information in a file in the database 29. A spreadsheet application is employed to convert this file to a percent obscuration per day. In the preferred embodiment, to simplify data collection and analysis, the particle data for each image is added to all of the data for the previous images in the database 29 so that the stored information actually represents the integral, G(t), of the number of collected particles over time. To calculate the number of particles, F(t), falling on the disk 12 during any given interval, the computer 26 therefore calculates the derivative of G(t). Then, to calculate the particle fallout rate per unit area, R(t), on the disk 12, the computer calculates the derivative of F(t). Thus, R(t) is found by taking the second derivative of G(t).

During the operation of the system 10, the housing 14 is placed in an area where particle fallout is to be monitored, and the system 10 is actuated by energizing the disk drive motors 18 and 24, light source 20, camera 22 and computer 26. As the disk 12 slowly rotates, fallout particles will collect on the circumferential collection band 19 defined by the aperture 16. The camera 22 generates digital images of the radial sector of the disk 12 on which the microscope objective 34 is focused, and continuously inputs these to the frame grabber board 28. Once every revolution of the first drive motor 18 (e.g., once every minute), the disk 12 is radially shifted an incremental amount relative to the microscope objective 34 by the cam member 42 to change the radial portion of the disk 12 on which the microscope objective 34 is focused.

Every few seconds or less, the computer 26 samples the image data in the frame grabber board 28, and performs the particle analysis process illustrated in FIG. 7. Initially, the computer 26 will presumably not detect any particles on the disk 12. After a period of time, however, depending upon the cleanliness of the monitored area and the particle size sensitivity of the system elements, particles will be detected on the disk 12 and the computer 26 will categorize them by size, quantity and type. This information is collected in the database 29, and the post processing is carried out to determine various parameters, including the fallout rate per unit area for a given time frame, the total fallout per unit area as defined in terms of percent obscuration of the disk 12 by the particles, etc. In addition, if the computer 26 detects that the instantaneous fallout rate has increased beyond a maximum permissible rate, the computer will generate a suitable audible or visual (or other, e.g., audible) alarm to indicate this condition in virtually real-time.

Although the invention has been disclosed in terms of a preferred embodiment and variations thereon, it will be understood that numerous additional modifications and variations could be made thereto without departing from the scope of the invention as defined in the following claims. For example, although the preferred embodiment of the present invention employs motors to move the particle collection disk 12 relative to the camera 22, it should be understood that the same result could be obtained if the camera 22 is moved instead, and the disk 12 is held stationary. In this arrangement, the aperture 16 would be made larger to increase the particle collection area on the disk 12, and then the camera 22 would be continuously scanned beneath the surface of the disk 12 to image different portions thereof.

What is claimed is:

1. A system for detecting particle fallout comprising:
a) a housing;
b) a transparent surface disposed in said housing for collecting particle fallout;
c) a sized aperture disposed in a top of said housing, and positioned above first a portion of said surface for defining an area on said surface for collecting particle fallout;
d) an optical detector disposed in said housing beneath said surface for generating an image of particles collected on said surface; and e) a computer for receiving an image from said optical detector, said computer including means for detecting, counting and sizing particles on said surface from said image.

2. The system of claim 1, further comprising:

f) a first drive motor for rotating said surface to increase the area on said surface which is exposed to particle fallout through said aperture.

3. The system of claim 2, wherein said surface comprises a top surface of a transparent, smooth, flat disk.

4. The system of claim 2, further comprising means for laterally moving said detector relative to said surface to provide random image sampling of said surface by said detector.

5. The system of claim 4, wherein said means for moving further comprises a second drive motor for scanning said surface back and forth relative to said detector.

6. The system of claim 1, further comprising a light source disposed in said housing for illuminating said surface.

7. The system of claim 6, wherein said light source further comprises a first light source for back lighting said surface, and a second light source for front lighting said surface.

8. The system of claim 1, wherein said detector comprises a CCD camera.

9. The system of claim 8, further including a microscope objective disposed in said housing, and focused on said surface for providing a magnified image of said surface to said camera.

10. The system of claim 9, further including means for adjusting a distance between said microscope objective and said surface to adjust the focus of an image provided to said camera.

11. The system of claim 1, wherein said housing is opaque, and said detector is disposed beneath a second portion of said surface generally opposite said first portion of said surface, and away from said sized aperture to reduce exposure of said detector to ambient light through said aperture; and wherein said system further includes:

a first drive motor for rotating said surface to increase the area on said surface which is exposed to particle fallout through said aperture, and for moving said first portion of said surface over said detector so that said detector can obtain an image of said first portion.

12. The system of claim 11, further comprising means for laterally moving said detector relative to said surface to provide random image sampling of said surface by said detector.

13. The system of claim 12, wherein said means for laterally moving further comprises a second drive motor and a cam element for scanning said surface back and forth relative to said detector.

14. The system of claim 1, wherein said computer further includes means for storing particle size and number data for a plurality of images of said surface, and determining a particle fallout rate from said stored size and number data for a plurality of images of said surface.

15. The system of claim 14, wherein said computer further includes means for detecting a particle fallout rate which exceeds a maximum allowable rate, and generating an indication that said maximum allowable rate has been exceeded.

16. A system for detecting particle fallout comprising:

a) a housing;

b) a transparent, smooth, flat disk disposed in said housing having a top surface for collecting particle fallout;

c) a sized aperture formed in a top of said housing over a first portion of said disk for defining an area on said disk for collecting particle fallout;

d) an optical detector disposed in said housing beneath a second portion of said disk for generating an image of particles collected on said disk;

e) a first drive motor for rotating said disk to increase the area on said disk which is exposed to particle fallout through said aperture, and for moving said first portion of said disk over said optical detector;

f) a computer for receiving an image from said optical detector, said computer including means for detecting, counting and sizing particles on said disk from said image; and g) a light source disposed in said housing for illuminating said disk.

17. The system of claim 16, further comprising means for laterally moving said detector relative to said disk to provide random image sampling of said disk by said detector.

18. The system of claim 17, wherein said means for laterally moving further comprises a second drive motor and a cam for scanning said disk back and forth relative to said detector.

19. The system of claim 16, wherein said computer further includes means for storing particle size and number data for a plurality of images of said disk, and determining a particle fallout rate from said stored size and number data for a plurality of images of said surface.

20. The system of claim 19, wherein said computer further includes means for detecting a particle fallout rate which exceeds a maximum allowable rate, and generating an indication that said maximum allowable rate has been exceeded.

21. A method for detecting particle fallout comprising:

a) positioning a flat transparent surface for collecting particle fallout in an area where particle fallout is to be detected;

b) obtaining an optical image of said surface with an optical detector;

c) analyzing said optical image with an image processing algorithm to detect, count, size and classify particles collected on said surface;

d) obtaining additional images of said surface with said optical detector;

e) analyzing said additional images with said image processing algorithm to detect, count, size and classify particles collected on said surface; and f) accumulating particle data for each of said images in a database.

22. The method of claim 21, further comprising the step of determining a particle fallout rate on said surface through mathematical differentiation by calculating the second derivative of said accumulated particle data.

23. The method of claim 22, further comprising the step of generating an indication if said determined particle fallout rate exceeds a predetermined rate.

24. The method of claim 21, wherein said step of positioning further comprises disposing a transparent disk in a housing with a first portion of said disk beneath an aperture in said housing, and positioning said housing in an area where particle fallout is to be measured.

25. The method of claim 24, further comprising the steps of positioning said optical detector in said housing beneath a second portion of said disk, away from said aperture and rotating said disk to periodically move said first portion of said disk over said optical detector.

26. The method of claim 25, further comprising the step of laterally moving said disk relative to said detector to enable said detector to obtain images of a plurality of radially spaced portions of said disk.

* * * * *